United States Patent
Takamura et al.

(10) Patent No.: US 9,334,477 B2
(45) Date of Patent: May 10, 2016

(54) METHOD FOR COLLECTING NUCLEATED RED BLOOD CELLS VIA DENSITY-GRADIENT CENTRIFUGATION UTILIZING CHANGES IN BLOOD CELL DENSITY

(75) Inventors: Yuzuru Takamura, Nomi (JP); Kotaro Idegami, Nomi (JP); Mieko Kogi, Nonoichi (JP); Haruo Takabayashi, Ishikawa (JP)

(73) Assignees: JAPAN ADVANCED INSTITUTE OF SCIENCE AND TECHNOLOGY, Nomi-Shi (JP); KANAZAWA INSTITUTE OF TECHNOLOGY, Nonoichi-Shi (JP); KANAZAWA MEDICAL UNIVERSITY, Kahoku-Gun (JP)

( * ) Notice: Subject to any disclaimer, the term of this patent is extended or adjusted under 35 U.S.C. 154(b) by 561 days.

(21) Appl. No.: 13/700,947

(22) PCT Filed: Feb. 21, 2011

(86) PCT No.: PCT/JP2011/054414
§ 371 (c)(1),
(2), (4) Date: Nov. 29, 2012

(87) PCT Pub. No.: WO2012/023298
PCT Pub. Date: Feb. 23, 2012

(65) Prior Publication Data
US 2013/0072402 A1    Mar. 21, 2013

(30) Foreign Application Priority Data
Aug. 20, 2010 (JP) .................. 2010-185608

(51) Int. Cl.
| | | |
|---|---|---|
| B03D 3/00 | (2006.01) | |
| C12N 5/078 | (2010.01) | |
| C12N 5/00 | (2006.01) | |
| G01N 33/49 | (2006.01) | |
| G01N 33/80 | (2006.01) | |
| C12Q 1/68 | (2006.01) | |

(52) U.S. Cl.
CPC ............ *C12N 5/0641* (2013.01); *B03D 3/00* (2013.01); *C12N 5/0087* (2013.01); *C12Q 1/6806* (2013.01); *C12Q 1/6883* (2013.01); *G01N 33/491* (2013.01); *G01N 33/80* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,432,054 A | 7/1995 | Saunders et al. | |
| 5,489,386 A * | 2/1996 | Saunders | G01N 33/491 |
| | | | 210/514 |
| 5,714,325 A * | 2/1998 | Bianchi | 435/6.16 |
| 6,210,889 B1 * | 4/2001 | Drouin | C12N 5/0634 |
| | | | 435/2 |
| 2005/0214758 A1 | 9/2005 | Yura et al. | |

FOREIGN PATENT DOCUMENTS

| | | |
|---|---|---|
| EP | 0778944 B1 * | 6/1997 |
| EP | 0 778944 B1 * | 11/1999 |
| JP | 9-509312 A | 9/1997 |
| JP | 11-502106 A | 2/1999 |
| WO | WO 96/27420 A1 | 9/1996 |
| WO | WO 03/050532 A1 | 6/2003 |

OTHER PUBLICATIONS

Ganshirt et al., "Enrichment of Fetal Nucleated Red Blood Cells from the Maternal Circulation for Prenatal Diagnosis: Experiences with Triple Density Gradient and MACS Based on More than 600 Cases", Fetal Diagnosis and Therapy, vol. 13, No. 5, p. 276 (1998).*
Percoll Product Sheet, p. 1-12, accessed at https://www.gelifesciences.com/gehcls_images/GELS/Related%20Content/Files/1314823637792/litdoc28903834_20130320212446.pdf on (Jan. 23, 2014).*
Polymorphprep Product Brochure, p. 1-3, accessed at http://www.axis-shield-density-gradient-media.com/Pmpp.pdf on (Jan. 23, 2014).*
Certificate dated Sep. 14, 2010 regarding publication date of Harada reference.
International Search Report, dated Mar. 29, 2011, issued in PCT/2011/054414.
Shun Harada, "Collection and Purification of Nucleated Red Blood Cells Via Density-Gradient Centrifugation", Kanazawa Institute of Technology, College of Informatics and Human communication, Department of Biosciences and Informatics, p. 34, Feb. 23, 2010.

* cited by examiner

*Primary Examiner* — Ralph Gitomer
(74) *Attorney, Agent, or Firm* — Birch, Stewart, Kolasch & Birch, LLP

(57) ABSTRACT

Method for concentrating and collecting small quantities of fetal nucleated red blood cells contained in the maternal blood. The method for concentrating and collecting nucleated red blood cells from the maternal blood comprises: (i) subjecting the maternal blood to a first density-gradient centrifugation and collecting a cell fraction containing nucleated red blood cells; (ii) treating the cell fraction containing nucleated red blood cells so as to selectively changes the density of the nucleated red blood cells from that of the white blood cells; and (iii) subjecting the treated cell fraction containing the nucleated red blood cells to a second density-gradient centrifugation so as to collect a fraction containing nucleated red blood cells.

7 Claims, 10 Drawing Sheets
(3 of 10 Drawing Sheet(s) Filed in Color)

| RUN | | 1 | 2 | 3 | 4 | 5 |
|---|---|---|---|---|---|---|
| Blood | | Maternal blood | Maternal blood | Maternal blood | Maternal blood | Maternal blood |
| WBC band after centrifugation | | Present | Present | Present | Present | Present |
| Percentage of WBC removal with hypertonic Percoll relative to isosmotic Percoll | 383 mOsm | 60% | - | - | - | - |
| | 353 mOsm | 94 % | 94 % | - | - | - |
| | 330 mOsm | - | - | - | 98 % | - |
| | 322 mOsm | 98 % | 97 % | 99.1 % | - | - |
| | 312 mOsm | - | - | - | 99 % | 98 % |
| | 308 mOsm | 99.9 % | - | 99.7 % | - | - |

METHOD FOR COLLECTING NUCLEATED RED BLOOD CELLS VIA DENSITY-GRADIENT CENTRIFUGATION UTILIZING CHANGES IN BLOOD CELL DENSITY

This application is a National Stage application filed under Rule 371 based upon PCT/JP2011/054414 filed Feb. 21, 2011.

TECHNICAL FIELD

The present invention relates to a method for cell separation. More particularly, the present invention relates to a method for separating nucleated red blood cells from the blood.

BACKGROUND ART

For the purpose of prenatal genetic diagnosis, amniotic diagnosis has heretofore been conducted primarily by sampling amniotic fluid via amniocentesis and inspecting chromosomes of the fetal cells in the amniotic fluid. Conventional prenatal genetic diagnostic techniques suffered from the serious problems of a risk of miscarriage in addition to physical and mental stresses on mothers. Under such circumstances, fetal cells (fetal nucleated red blood cells) were found to migrate in the blood circulating in the mother's body. If fetal nucleated red blood cells contained in the maternal blood are selectively collected and the genes of the fetus are analyzed, prenatal diagnosis can be safely carried out without a risk of miscarriage. Such technique enables fetal gene diagnosis at an early stage of pregnancy, which can lead to early treatment. Approximately 5,000,000 cases of prenatal genetic diagnosis are conducted every year on a global scale. If such safe genetic diagnostic technique can be put to practical use, safe techniques can occupy a high share of the global market. However, it is not easy to collect fetal nucleated red blood cells because such cells are said to exist in amounts as small as about 1 cell in 1 ml of the maternal blood. A collection method involving the use of an antibody that recognizes a special structure of the nucleated red blood cell surface (i.e., an antigen-antibody reaction), a method comprising allowing fluorescence-labeled nucleated red blood cells to flow in a liquid, allowing such blood cells to pass through the laser beam focal point, and assaying fluorescence emitted by blood cells to collect cells (i.e., fluorescence activated cell sorting (FACS)), and other techniques have been implemented in research institutes all over the world. However, all such techniques have been insufficient. As a method for collecting nucleated red blood cells with high assuredness, a method comprising analyzing an image observed under an optical microscope and collecting the nucleated red blood cells detected can be employed. According to the FDD-MB® (Fetal DNA diagnosis from maternal blood) project of Takabayashi (Kanazawa Medical University), at present, fetal nucleated red blood cells are separated from the maternal blood via density-gradient centrifugation using Percoll to prepare samples and automatically processed to collect NRBC (Haruo Takabayashi, *Idenshi Igaku* (Gene & Medicine), Vol. 5, No. 3, 2001, pp. 10-11; Haruo Takabayashi, *Idenshi Igaku* (Gene & Medicine), Vol. 5, No. 3, 2001, pp. 28-34 2). Detection of the nucleated red blood cells via imaging disadvantageously necessitates a long period of time.

Rare cells have heretofore been separated by density-gradient centrifugation using Ficoll, Percoll, Polymorphprep, or the like (US Patent Publication No. 2003/0134416; US Patent Publication No. 2004/0142463; U.S. Pat. No. 5,714,325; U.S. Pat. No. 6,949,355; U.S. Pat. No. 7,166,443; WO International Publication No. 2008/048931). When such separation reagent is used alone, disadvantageously, nucleated red blood cells cannot be completely separated because their density (specific gravity) is similar to that of white blood cells and some other red blood cells (i.e., 1.07-1.08).

SUMMARY OF THE INVENTION

The present invention provides a method for separating a small amount of nucleated red blood cells contained in the maternal blood from white blood cells. Even if density-gradient centrifugation is carried out with the use of Percoll exhibiting the highest concentration efficiency among Ficoll, Percoll, Polymorphprep, and the like that have heretofore been used, nucleated red blood cells are secreted into a fraction having a specific gravity similar to that of most white blood cells, and as many as $1\times10^6$ white blood cells were found to remain in a fraction containing abundant nucleated red blood cells. This occurs because the nucleated red blood cells cannot be completely separated from white blood cells or some other red blood cells due to the similar density (approximately 1.07 to 1.095). White blood cells remaining in a fraction containing abundant nucleated red blood cells after centrifugation would interfere with subsequent procedures, such as separation of red blood cells using a chip or imaging. Further, the number of white blood cells contaminating such fraction tends to increase with the elapse of time after blood sampling. Thus, it also serves as a factor for determining the duration during which a blood sample can be stored. Accordingly, a way of removing most red blood cells, and, in particular, white blood cells, when concentrating nucleated red blood cells in the maternal blood would be an object to be attained.

The present inventors have conducted concentrated studies regarding a method for concentrating and collecting nucleated red blood cells from the maternal blood via density-gradient centrifugation. Nucleated red blood cells were known to have intermediate properties between those of white blood cells and red blood cells. In particular, nucleated red blood cells were known to exhibit a white-blood-cell-like density to Percoll. The present inventors discovered that the density of nucleated red blood cells would be changed by Ficoll and Polymorphprep (PMP), as in the case of red blood cells. Thus, density-gradient centrifugation may be first carried out by the Percoll method, which would not change the density of the nucleated red blood cells to remove most red blood cells; the Ficoll solution or PMP solution, which would change the density of the nucleated red blood cells, may be allowed to react with the nucleated red blood cells to change the density thereof; and density-gradient centrifugation may be carried out again. Thus, nucleated red blood cells can be separated from white blood cells and efficiently concentrated. This has led to the completion of the present invention.

Specifically, the present invention is as follows.

[1] A method for concentrating and collecting nucleated red blood cells from the maternal blood comprising:

(i) subjecting the maternal blood to a first density-gradient centrifugation and collecting a cell fraction containing nucleated red blood cells;

(ii) treating the cell fraction containing nucleated red blood cells to selectively changes the density of the nucleated red blood cells so as not to overlap that of the white blood cells; and (iii) subjecting the treated cell fraction containing the nucleated red blood cells to a second density-gradient centrifugation so as to collect a fraction containing nucleated red blood cells.

[2] The method for concentrating and collecting nucleated red blood cells according to [1], wherein the treatment of step (ii) for selectively changing the density of the nucleated red blood cells is treatment of a fraction containing nucleated red blood cells with a solution that is more hypertonic or hypotonic than the solution used for the first density-gradient centrifugation.

[3] The method for concentrating and collecting nucleated red blood cells according to [2], wherein the medium used for the first density-gradient centrifugation of step (i) is isosmotic with the nucleated red blood cells, the treatment of step (ii) is carried out with the use of a hypertonic solution, and the medium used for the second density-gradient centrifugation of step (iii) is isosmotic with the hypertonic solution used in step (ii).

[4] The method for concentrating and collecting nucleated red blood cells according to any of [1] to [3], wherein a solution capable of selectively changing the density of the nucleated red blood cells is used as a medium for the second density-gradient centrifugation and step (ii) is carried out simultaneously with step (iii).

[5] The method for concentrating and collecting nucleated red blood cells according to [4], wherein a hypertonic or hypotonic solution capable of selectively changing the density of the nucleated red blood cells is used as a medium for the second density-gradient centrifugation and step (ii) is carried out simultaneously with step (iii).

[6] The method for concentrating and collecting nucleated red blood cells according to any of [1] to [5], wherein step (i) comprises collecting the blood cells having a density range of 1.070 to 1.095 g/ml.

[7] The method for concentrating and collecting nucleated red blood cells according to any of [1] to [6], wherein step (ii) comprises changing the density of the nucleated red blood cells to be greater than 1.095 g/ml.

[8] The method for concentrating and collecting nucleated red blood cells according to any of [1] to [7], wherein the medium used for density-gradient centrifugation is selected from the group consisting of Percoll, Ficoll, sucrose, Nycodenz®, and OPTIPrep™.

[9] The method for concentrating and collecting nucleated red blood cells according to any of [1] to [8], wherein the medium used for the first density-gradient centrifugation is Percoll having an osmotic pressure of 280±30 mOsm, and the medium used for the second density-gradient centrifugation is Percoll having an osmotic pressure of 300 mOsm or higher.

[10] The method for concentrating and collecting nucleated red blood cells according to any of [1] to [8], wherein the medium used for the first density-gradient centrifugation is Percoll, and the medium used for the second density-gradient centrifugation comprises 13.8% (w/v) sodium diatrizoate and 8.0% (w/v) dextran 500 and has an osmotic pressure of 460±15 mOsm.

[11] The method for concentrating and collecting nucleated red blood cells according to any of [1] to [8], wherein the medium used for the second density-gradient centrifugation is Polymorphprep™.

[12] A method for concentrating and collecting nucleated red blood cells from the maternal blood comprising subjecting the maternal blood to a first density-gradient centrifugation using Percoll, collecting a cell fraction containing nucleated red blood cells, subjecting a cell fraction containing the nucleated red blood cells to a second density-gradient centrifugation using Polymorphprep™, and collecting a fraction containing the nucleated red blood cells.

[13] The method for concentrating and collecting nucleated red blood cells according to any of [1] to [12], wherein the nucleated red blood cells are fetal nucleated red blood cells.

[14] A method of fetal DNA diagnosis performed with the use of nucleated red blood cells collected by the method according to any of [1] to [13].

[15] The method of fetal DNA diagnosis according to [14], wherein the fetal DNA diagnosis is carried out by a method selected from the group consisting of PCR, FISH (fluorescence in situ hybridization), PEP (primer extension preamplification), TaqMan® PCR, CGH (comparative genomic hybridization), PRINS (Primed in situ labeling), cell recycling, a DNA chip technique, and a combination of any thereof.

[16] A kit used for concentrating and collecting nucleated red blood cells from the maternal blood comprising:
(a) a medium for the first density-gradient centrifugation that is isosmotic with nucleated red blood cells;
(b) a solution that selectively changes the density of the nucleated red blood cells; and
(c) a medium for the second density-gradient centrifugation that is isosmotic with the solution of (b).

[17] A kit used for concentrating and collecting nucleated red blood cells from the maternal blood comprising:
(a) a medium for the first density-gradient centrifugation that is isosmotic with nucleated red blood cells; and
(b) a medium for the second density-gradient centrifugation comprising a solution that selectively changes the density of the nucleated red blood cells.

[18] The kit used for concentrating and collecting nucleated red blood cells according to [16] or [17], wherein the solution that selectively changes the density of the nucleated red blood cells is a solution for hypertonic treatment that is hypertonic to the nucleated red blood cells.

[19] The kit used for concentrating and collecting nucleated red blood cells according to any of [16] to [18], wherein the medium for density-gradient centrifugation is selected from the group consisting of Percoll, Ficoll, sucrose, Nycodenz®, and OPTIPrep™.

[20] A kit used for concentrating and collecting nucleated red blood cells from the maternal blood comprising Percoll used as a medium for the first density-gradient centrifugation and Polymorphprep™ used as a medium for the second density-gradient centrifugation.

[21] A kit used for concentrating and collecting nucleated red blood cells from the maternal blood comprising Percoll used as a medium for the first density-gradient centrifugation having an osmotic pressure of 280±30 mOsm and Percoll used as a medium for the second density-gradient centrifugation having an osmotic pressure of 420±30 mOsm.

[22] The kit used for concentrating and collecting nucleated red blood cells according to any of [16] to [21], wherein the nucleated red blood cells are fetal nucleated red blood cells.

According to the method of the present invention, the density of the nucleated red blood cells in the maternal blood is selectively changed when conducting density-gradient centrifugation. For example, a fraction containing concentrated fetal nucleated red blood cells and small amounts of white blood cells can be obtained from the maternal blood. Fetal nucleated red blood cells can be easily identified and isolated from such fraction, and prenatal diagnosis of a fetus can be carried out with the use of the isolated fetal nucleated red blood cells. When blood cells are identified and isolated based on the images of blood cells and nuclei, in particular, the total cell count is reduced, and white blood cells that can be mistaken for nucleated red blood cells are removed in the process of identification and isolation of the present invention. Such operations can significantly improve conditions in terms of the number and the duration of operations in the process of identification and isolation. When fetal diagnosis is carried out based on DNA information, the risk for misdiagnosis would increase upon contamination with white blood cells since white blood cells have DNA. Thus, removal of white blood cells conducted in the present invention could effectively reduce the risk for misdiagnosis and improve diagnostic quality. In general, the number of white blood cells having a density range that is the same as that of the nucleated red blood cells increases due to natural changes in the blood cell density with the elapse of time after maternal blood sampling. When conventional density-gradient centrifugation is performed, the number of white blood cells contaminating a fraction containing nucleated red blood cells increases with the elapse of time. According to the present invention, the density of the nucleated red blood cells is selectively changed not to overlap that of white blood cells. Accordingly, a fraction containing nucleated red blood cells free from white blood cells can be obtained. This is effective for prolonging the storage period until the processing is initiated after blood sampling. According to conventional techniques of conducting density-gradient centrifugation only once, further, nucleated red blood cells having the narrow density range, such as nucleated red blood cells having a density range of 1.075 to 1.085 g/ml, were collected in order to minimize contamination with white blood cells. However, the nucleated red blood cells are distributed across an extensive area. According to the present invention, nucleated red blood cells with a more extensive density range can be collected without being contaminated by white blood cells (FIG. 1), the number of total nucleated red blood cells increases, and the success rate of diagnosis or the quality thereof can be improved.

This description includes part or all of the content as disclosed in the description and/or drawings of Japanese Patent Application No. 2010-185608, which is a priority document of the present application.

BRIEF DESCRIPTION OF THE DRAWINGS

The patent or application file contains at least one color drawing. Copies of this patent or patent application publication with color drawing will be provided by the USPTO upon request and payment of the necessary fee.

In FIG. 1, the density range indicated as "Conventional range of collection" indicates the density range to be collected as a fraction containing nucleated red blood cells by a conventional technique comprising a single step of density-gradient centrifugation using a Percoll solution. The density range indicated as "Range of collection of the present invention" indicates the density range to be collected as a fraction containing nucleated red blood cells by the method of the present invention comprising two steps of density-gradient centrifugation.

FIG. 10 shows the percentage of white blood cells removed from a sample after density-gradient centrifugation using a hypertonic Percoll solution relative to the sample after centrifugation using an isosmotic Percoll solution when the maternal blood is subjected to density-gradient centrifugation with the use of an isosmotic Percoll solution and then with a hypertonic Percoll solution.

EMBODIMENTS FOR CARRYING OUT THE INVENTION

Figure 1:
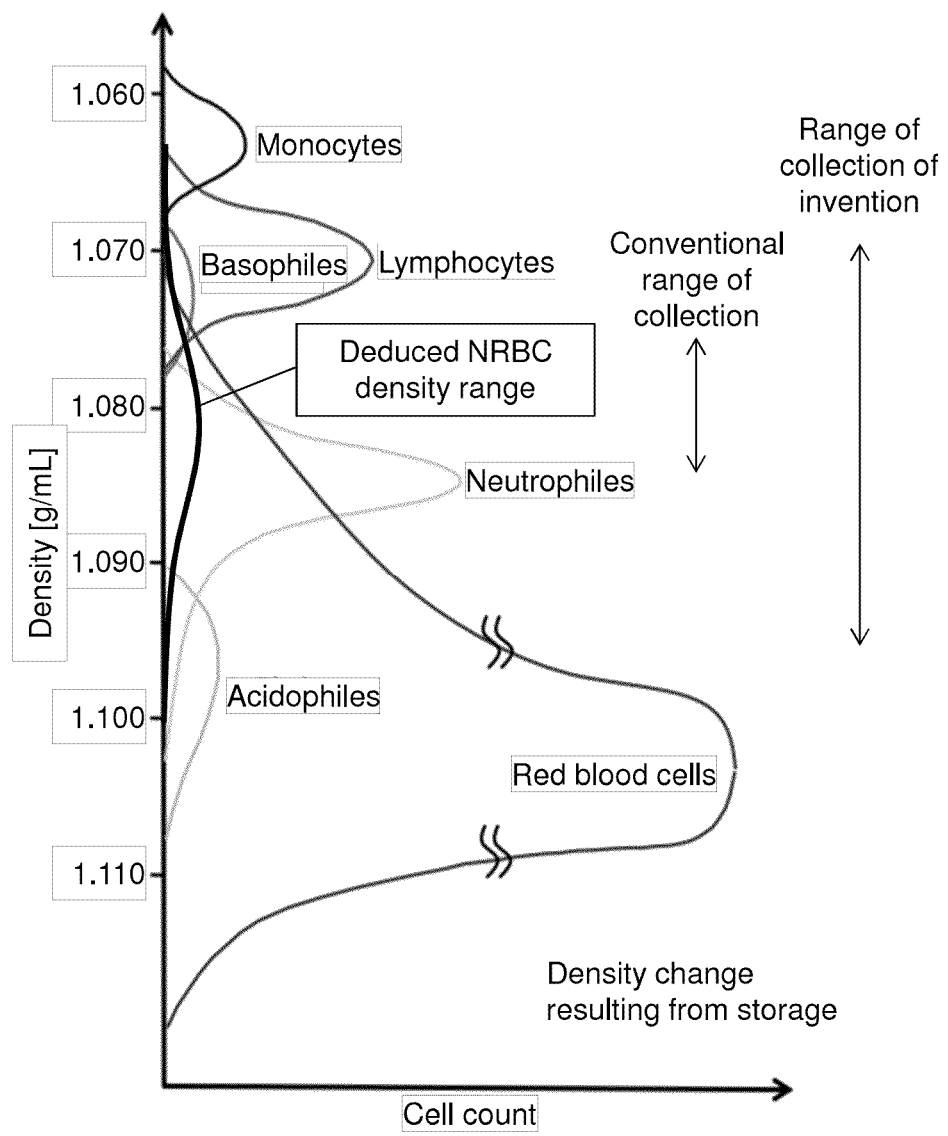
FIG. 1 shows density ranges of red blood cells, nucleated red blood cells (NRBC), and various white blood cells.

Hereafter, the present invention is described in detail.

In the present invention, the term "maternal blood" refers to the peripheral blood of a pregnant woman.

The maternal blood contains immature nucleated red blood cells (NRBC) and white blood cells derived from the fetus, in addition to white blood cells and mature red blood cells, such as acidophiles, neutrophiles, basophiles, monocytes, and lymphocytes derived from the mother. The maternal blood occasionally contains immature nucleated red blood cells derived from the mother. Fetal nucleated red blood cells appear in the maternal blood from approximately the 4th to 8th week of pregnancy. Accordingly, the present invention is targeted at women in the 4th to 8th week of pregnancy or thereafter, and samples are preferably obtained from pregnant women in the 4th to 37th week of pregnancy. The number of fetal nucleated red blood cells contained in the mother's peripheral blood is as low as about 1 cell in 1 ml of the maternal blood, and the number of fetal red blood cells in the maternal blood cells is about 1 cell per about $10^7$ to $10^9$ blood cells.

According to the method of the present invention, a fraction containing nucleated red blood cells in the maternal blood can be separated, and fetal nucleated red blood cells can be concentrated and collected. In the present invention, the term "red blood cells" refers to mature red blood cells, and such red blood cells are distinguished from nucleated red blood cells.

In the present invention, a procedure of concentration and collection comprises obtaining a fraction containing concentrated nucleated red blood cells from the maternal blood. Such procedure can also be expressed as concentration, collection, separation, or separation and collection. Most red blood cells existing in the maternal blood have been removed from a fraction containing concentrated nucleated red blood cells, and the number of white blood cells has fallen significantly. Preferably, substantially no white blood cells are contained. More preferably, no white blood cells are contained.

In general, about 10 nucleated red blood cells, about $4 \times 10^{10}$ red blood cells, and about $8 \times 10^7$ white blood cells are contained in 10 ml of the maternal blood (the peripheral blood of a pregnant woman), although there are differences between individuals. When a single step of density-gradient centrifugation using Percoll alone is carried out (i.e., a conventional technique), about 10 nucleated red blood cells, about $4 \times 10^6$ red blood cells, and about $1 \times 10^5$ to about $2 \times 10^7$ white blood cells are contained in a fraction containing nucleated red blood cells. In contrast, the fraction containing nucleated red blood cells obtained by the method of the present invention contains about 10 nucleated red blood cells, about $4 \times 10^6$ red blood cells, and about 10 to $5 \times 10^6$ white blood cells, although such amounts vary depending on conditions. Specifically, the number of white blood cells can be reduced to about one-tenth to one-ten millionth their original level by the method of the present invention, and it can be reduced to about half to one millionth of the level possible with a conventional technique.

When genes or chromosomes are analyzed with the use of fetal nucleated red blood cells, it is necessary to distinguish fetal nucleated red blood cells from other blood cells and to identify and isolate fetal nucleated red blood cells from among blood cells. For example, a method in which a blood smear is prepared using a glass slide, an optical microscopic image is obtained and analyzed, and fetal nucleated red blood cells are distinguished from maternal red blood cells and white blood cells via nuclear staining or morphological observation to identify and isolate the fetal nucleated red blood cells has been known. However, white blood cells have nuclei, and some of them have configurations similar to those of nucleated red blood cells. Thus, it was difficult to completely distinguish nucleated red blood cells from white blood cells via image analysis. When the maternal blood is subjected to image diagnosis without any processing, identification of nucleated red blood cells from among numerous blood cells is very time-consuming due to small amounts of fetal nucleated red blood cells. According to the present invention, most red blood cells can be removed from the maternal blood, white blood cells can be reduced by a significant level at least, and a fraction containing concentrated nucleated red blood cells, which preferably contains no white blood cells, can be obtained. As a result, nucleated red blood cells can be easily distinguished from other cells in the obtained fraction, and such cells can be identified and isolated. According to the method of the present invention, specifically, fetal nucleated red blood cells can be separated and collected from the maternal blood. When maternal nucleated red blood cells are contained in a fraction containing fetal nucleated red blood cells, maternal nucleated red blood cells can be easily distinguished from fetal nucleated red blood cells via analysis of DNA of nucleated red blood cells, and fetal nucleated red blood cells can be identified and isolated. A nucleated red blood cell fraction in the maternal blood may occasionally contain maternal nucleated red blood cells in amounts approximately the same as those of fetal nucleated red blood cells (Sekizawa, A. et al., Prenat. Diagn. 2007, 27: 846-848). According to the method of the present invention, nucleated red blood cells can be concentrated and collected from all cells even when maternal nucleated red blood cells are contained. This remarkably increases the number of nucleated red blood cells in the obtained fraction. Thus, fetal nucleated red blood cells can be easily distinguished from maternal nucleated red blood cells, and such cells can be easily identified and isolated from such fraction.

The densities of maternal red blood cells are as follows: about 1.070 to 1.120 g/ml of red blood cells; about 1.090 to 1.110 g/ml of acidophiles; about 1.075 to 1.100 g/ml of neutrophiles; about 1.070 to 1.080 g/ml of basophiles; about 1.060 to 1.080 g/ml of lymphocytes; and about 1.060 to 1.070 g/ml of monocytes (FIG. 1). In contrast, the fetal nucleated red blood cell density is about 1.065 to 1.095 g/ml. The density range of fetal nucleated red blood cells is the same as that of the maternal red blood cells and some white blood cells. The blood cell density can be determined by, for example, density-gradient centrifugation using Percoll. The density at 20° C. is employed, unless otherwise specified.

At the outset, the maternal blood is subjected to density-gradient centrifugation to separate the blood cells contained in the maternal blood based on densities. In the present invention, the initial density-gradient centrifugation is occasionally referred to as the "first step of density-gradient centrifugation." In general, the density of a solution in a centrifuge tube is lowered from the bottom toward the top, a sample is centrifuged therein, and target substances or cells form layers in regions at a given density in the solution. With the utilization of such properties, a target product is fractionated according to a technique of density-gradient centrifugation. A fraction containing nucleated red blood cells can be separated from a fraction containing no nucleated red blood cells via density-gradient centrifugation. After density-gradient centrifugation is carried out, blood cells within the density range including nucleated red blood cells are collected, and a fraction containing concentrated fetal nucleated red blood cells can then be obtained. According to the study conducted by the present inventors, the density of the nucleated red blood cells is about 1.065 to 1.095 g/ml. Thus, blood cells having a density range of 1.060 to 1.100 g/ml, preferably 1.070 to 1.095 g/ml, more preferably 1.070 to 1.085 g/ml, and particularly preferably 1.075 to 1.085 g/ml are collected. By performing such density-gradient centrifugation, a fraction containing nucleated red blood cells can be separated from a fraction containing white blood cells having a low density and a fraction containing red blood cells or acidophiles having a high density. In particular, most of the maternal red blood cells existing in the largest quantities can be removed. Cells can be collected with the use of a pipette, for example. In such a case, the rate of recovery for nucleated red blood cells increases as the density range for collection is enlarged. As described above, part of the density range of fetal nucleated red blood cells is the same as that of maternal red blood cells or white blood cells. This increases the number of maternal blood cells contaminating the fetal nucleated red blood cells. According to the present invention, even if nucleated red blood cells are contaminated with blood cells in the maternal blood as a result of the first step of density-gradient centrifugation described above, such contaminating blood cells can be removed from a fraction containing fetal nucleated red blood cells in the subsequent step of separation.

A medium used for the first density-gradient centrifugation may have a density of about 1.050 to 1.100 g/ml at 20° C. Examples thereof that can be used include Percoll (a colloidal silica product coated with polyvinyl pyrrolidone), Ficoll (a sucrose-epichlorohydrin copolymer), sucrose, Nycodenz® (N,N'-bis(2,3-dihydroxypropyl)-5-[N-(2,3-dihydroxypropyl)acetamido]-2,4-6-triiodo-isophthalamide), and OPTIPrep™ (an aqueous solution of 60% iodixanol). Commercial products, such as Percoll™ (Sigma-Aldrich Japan K.K.), Ficoll™-Paque PLUS, Ficoll-Hypaque (Pharmacia Biotech, Inc.), Histopaque (Sigma-Aldrich Japan K.K.), and Lymphoprep® (Nikomed), can be used as Percoll and Ficoll, respectively. Use of Percoll is particularly preferable. At the time of the first density-gradient centrifugation, it is necessary that the density (the specific gravity) of the nucleated red blood cells does not change when blood cells are mixed with a medium for density-gradient centrifugation. Thus, the osmotic pressure of the medium is adjusted to be isosmotic with that of blood cells, such as nucleated red blood cells. In such a case, the osmotic pressure is about 280 mOsm. The osmotic pressure can be adjusted using, for example, sodium chloride. When Percoll is used as a medium, a sodium chloride solution or phosphate buffered saline that is highly concentrated so as to have an osmotic pressure higher than that of physiological saline in advance may be mixed with Percoll so as to bring the osmotic pressure thereof to the same level as that of physiological saline (i.e., about 280 mOsm, such as 280±20 mOsm or 280±10 mOsm). Also, the density of a medium used can be adequately adjusted. When Percoll is used, for example, the density of Percoll is adjusted to prepare a 1.070 g/ml Percoll solution and a 1.095 g/ml Percoll solution, these solutions are superposed on top of one another, and the resultant is subjected to centrifugation. In such a case, a layer of a fraction containing nucleated red blood cells is generated between the 1.070 g/ml layer and the 1.095 g/ml layer, and the resulting layer may be collected. In this case, the maternal red blood cells settle to the bottom due to the high density, and many white blood cells generate layers on the medium surface due to the low density. Thus, such layers can be separated from layers comprising nucleated red blood cells alone. Alternatively, for example, a 1.095 g/ml Percoll solution may be used alone without performing superposition. In this case, the maternal red blood cells settle to the bottom, and white blood cells and nucleated red blood cells form layers on medium surfaces. While nucleated red blood cells cannot be separated from white blood cells, nucleated red blood cells can be separated from white blood cells in the subsequent step of separation of the present invention.

Centrifugation may be carried out by superposing the maternal blood on the medium. Centrifugation is carried out at, for example, 1,440 to 2,400 G, preferably 750 to 1800 G, and more preferably 780 G for 20 to 40 minutes. A centrifuge tube used for density-gradient centrifugation can be, for example, a commercially available disposable centrifuge tube.

Subsequently, the density of nucleated red blood cells among blood cells contained in a fraction containing nucleated red blood cells (i.e., nucleated red blood cells, (anuclear) mature red blood cells, and white blood cells) collected via density-gradient centrifugation is selectively changed. The density of anuclear red blood cells may be changed simultaneously, and it is preferable that the density thereof be selected in such a manner that the density of white blood cells is not significantly changed. The density of nucleated red blood cells can be selectively changed by bringing a fraction collected via density-gradient centrifugation into contact with a solution capable of changing the density of the nucleated red blood cells. A solution capable of changing the density of the nucleated red blood cells can be, for example, a solution that is hypertonic or hypotonic to nucleated red blood cells. A fraction containing nucleated red blood cells is brought into contact with a hypertonic or hypotonic solution to treat the nucleated red blood cells therewith. Thus, the density of the nucleated red blood cells can be selectively changed. In nucleated red blood cells, water easily migrates through a membrane. When such blood cells are brought into contact with a hypertonic solution (i.e., a solution with an osmotic pressure higher than that of physiological saline), accordingly, water is discharged from the blood cells, and the density of the blood cells is increased. When the blood cells are brought into contact with a hypotonic solution (i.e., a solution with an osmotic pressure lower than that of physiological saline), water invades into the blood cells, and the density thereof is decreased. Meanwhile, the density of white blood cells is less likely to change even if they are brought into contact with a hypertonic or hypotonic solution. The density of the nucleated red blood cells in the fraction collected via density-gradient centrifugation is differentiated from that of white blood cells contaminating such fraction. Preferably, the nucleated red blood cells are mixed with a hypertonic solution to increase the density of the nucleated red blood cells. When the fraction containing nucleated red blood cells is contaminated with mature red blood cells, such red blood cells exhibit behavior similar to that of nucleated red blood cells when treated with a hypertonic or hypotonic solution, and such red blood cells are included in the same fraction containing nucleated red blood cells in the end. Since mature red blood cells can be easily distinguished from nucleated red blood cells based on morphological observation or nuclear staining, such cells would not impede subsequent gene analysis or other procedures unless the amount thereof is excessive.

A sodium chloride solution or sucrose solution may be used for changing the density of the nucleated red blood cells. When cells are subjected to hypertonic treatment, for example, the fraction containing nucleated red blood cells collected via the first step of density-gradient centrifugation may be treated with a hypertonic solution with an osmotic pressure exceeding 280 mOsm (e.g., 300 mOsm or higher, preferably 308 mOsm or higher, and more preferably 310 mOsm or higher; 300 to 330 mOsm, preferably 308 mOsm to 330 mOsm, and more preferably 310 to 330 mOsm; or 350 to 600 mOsm, and preferably 400 to 450 mOsm). For example, cells may be mixed with a solution with a sodium chloride content exceeding 0.9%, preferably 1.0 to 2.0%, and more preferably 1.0 to 1.5%, and the resultant may then be allowed to stand for several minutes to several tens of minutes. If the cells are allowed to stand for an excessively long period of time, the white blood cell density is also changed. It is accordingly important to select an adequate duration. It should be noted that the cell density changes in accordance with the properties of a solution used for the second centrifugation during the second centrifugation. The osmotic pressure and the duration are regulated, so as to attain adequate results after the second centrifugation.

Also, substances capable of binding to the nucleated red blood cells and changing the density of the same may be bound to the membranes of the nucleated red blood cells to selectively change the density of the nucleated red blood cells. Examples of substances capable of changing the density of the nucleated red blood cells include dextran and derivatives thereof. An example of dextran is dextran 500. Examples of dextran derivatives include dextran sulfate and carboxymethyl dextran. In order to allow dextran to bind to a cell, for example, dextran may be added to a fraction containing nucleated red blood cells to bring the dextran concentration to 1 to 20% (w/v), and preferably 2 to 15% (w/v) therein.

The density of the nucleated red blood cells in the fraction collected via density-gradient centrifugation is selectively changed, and density-gradient centrifugation is then carried out again. In the present invention, such second process of density-gradient centrifugation may be occasionally referred to as the "second density-gradient centrifugation." A medium used for the second density-gradient centrifugation can be the same as a medium that can be used for the first density-gradient centrifugation. The medium that is actually used for the first density-gradient centrifugation may be used. In such a case, the osmotic pressure of the medium is preferably regulated at a level equivalent to that of a solution used when selectively changing the density of the nucleated red blood cells in the fraction collected via density-gradient centrifugation.

Since the density of the nucleated red blood cells is selectively changed from that of white blood cells, nucleated red blood cells can be separated from white blood cells via density-gradient centrifugation. In such a case, the density may be changed so as not to overlap the density range of the cell layer collected as a fraction containing nucleated red blood cells via the first density-gradient centrifugation. When cells having a density range of 1.070 to 1.095 g/ml are collected as a fraction containing nucleated red blood cells after the first density-gradient centrifugation, for example, the cells may be treated with a hypertonic or hypotonic solution to bring the density to a level lower than 1.070 g/ml or higher than 1.095 g/ml. When cells having a density range of 1.070 to 1.080 g/ml are collected as a fraction containing nucleated red blood cells after the first density-gradient centrifugation, similarly, the cells may be treated with a hypertonic or hypotonic solution to bring the density to a level lower than 1.070 g/ml or higher than 1.080 g/ml. After centrifugation, a blood cell layer within a density range that includes nucleated red blood cells at various densities may be collected, and a fraction containing large quantities of concentrated nucleated red blood cells can be obtained. The blood cell density changes during the second centrifugation. In order to maximize the selectivity, the duration of the second centrifugation is also important. The duration of the second centrifugation is 10 to 60 minutes, and preferably 20 to 40 minutes, including the duration of treatment for changing the density when a hypertonic solution of 420 mOsm is used, although the duration varies depending on the solution used for changing the density. When a hypertonic solution of 300 mOsm or higher is used, the duration is 10 to 60 minutes, and preferably 20 to 40 minutes, including the duration of treatment for changing the density.

The medium described above, which is capable of selectively differentiating the density of the nucleated red blood cells, can also be used as a medium for the second density-gradient centrifugation. In such a case, a fraction containing nucleated red blood cells collected via the first density-gradient centrifugation on a medium may be subjected to washing according to need, the resultant may be superposed on a medium for the second density-gradient centrifugation, and the second density-gradient centrifugation may then be initiated. Use of such medium enables performance of a step of changing the density of the nucleated red blood cells simultaneously with the second density-gradient centrifugation, following the first density-gradient centrifugation. The term "simultaneous" used herein refers to a situation in which the density is changed and density-gradient centrifugation is carried out without collecting blood cells and the like. For example, a Percoll solution that is hypertonic to nucleated red blood cells may be prepared, a fraction containing nucleated red blood cells may be superposed on such hypertonic Percoll solution, and the resultant may then be subjected to density-gradient centrifugation. The osmotic pressure can be regulated by the amount of NaCl added, and it is higher than 280 mOsm. For example, it is 300 mOsm or higher, preferably 308 mOsm or higher, and more preferably 310 mOsm or higher. Specifically, it is 300 to 330 mOsm, preferably 308 mOsm to 330 mOsm, and more preferably 310 to 330 mOsm. Alternatively, it is 350 to 600 mOsm, and preferably 400 to 450 mOsm. In this case, Polymorphprep™ (AXIS-SHIELD) may be used. Polymorphprep is a medium containing 13.8% (w/v) sodium diatrizoate and 8.0% (w/v) dextran 500. The osmotic pressure thereof is 460±15 mOsm, and the density is 1.113 0.001 g/ml at 20° C. Since Polymorphprep is hypertonic to nucleated red blood cells, it can increase the density of the nucleated red blood cells. Polymorphprep contains dextran. Accordingly, dextran is capable of binding to the nucleated red blood cell membrane and changing the density of the nucleated red blood cells. Specifically, a fraction containing fetal nucleated red blood cells collected after the first step of density-gradient centrifugation is superposed on the Polymorphprep solution. Nucleated red blood cells in the aforementioned fraction are precipitated at the bottom in the fraction during centrifugation, the blood cells are brought into contact with the Polymorphprep solution as an underlying layer, and this changes the density. Nucleated red blood cells can thus be separated from white blood cells. Since nucleated red blood cells are precipitated at the bottom of the centrifuge tube, they can be easily collected.

According to the method comprising two steps, blood cells that are evenly distributed in the upper layer begin to settle after centrifugation is initiated, and the density is changed upon contact with the lower layer. Accordingly, the period during which blood cells existing in an upper region of the upper layer are in contact with the solution that changes the density is shorter than that during which blood cells existing in a lower region of the upper layer are in contact therewith. This disadvantageously generates variations in the results. When the method is carried out in three steps comprising mixing the cells with a solution with a regulated osmotic pressure to change the cell density before the second density-gradient centrifugation, the durations required for changing the density can be precisely maintained at a constant level. This improves the reproducibility.

A fraction obtained by such method contains highly concentrated fetal nucleated red blood cells. The density of fetal nucleated red blood cells is much higher than that of fetal nucleated red blood cells in the maternal blood before treatment. For example, the number of nucleated red blood cells relative to the number of all blood cells in the fraction obtained by the method of the present invention is 4,000 to tens of thousands times greater than the number of cells in the original maternal blood.

The fetal nucleated red blood cells are identified and isolated from the resulting fraction containing highly concentrated nucleated red blood cells, and DNA or chromosome information on a fetus can be obtained with the use of such fetal nucleated red blood cells. Based on such DNA or chromosome information, prenatal diagnosis of a fetus is carried out. The term "DNA information" used herein refers to DNA sequence information such as that regarding DNA polymorphisms typified by single nucleotide polymorphisms (SNPs). The term "chromosome information" refers to information regarding chromosomal abnormality such as a trisomy. When the fraction comprises fetal nucleated red blood cells only, such cells may be subjected to prenatal diagnosis without any processing. When the fraction comprises red blood cells and white blood cells derived from the maternal blood, nucleated red blood cells are identified and, according to need, isolated from the blood cells in the fraction. The identified and isolated fetal nucleated red blood cells can be subjected to DNA analysis at a single cell level by PCR, FISH (fluorescence in situ hybridization), PEP (primer extension preamplification), TaqMan® PCR, CGH (comparative genomic hybridization), PRINS (Primed in situ labeling), cell recycling, a DNA chip technique, or a method comprising any thereof in combination.

For example, the obtained fraction containing nucleated red blood cells is applied to a glass slide to prepare a smear sample, the resulting smear sample is stained via May-Grunwald Giemsa staining or other means according to need, and an image thereof is prepared. Based on configurations or stained conditions of the blood cells, nucleated red blood cells on a glass slide can be identified. The thus-identified nucleated red blood cells can be subjected to gene or chromosome analysis via FISH (fluorescence in situ hybridization) on a glass slide. Also, genes can be isolated from the identified nucleated red blood cells, and mutations such as SNP can be analyzed. Such analysis can be performed in accordance with the method described in, for example, Haruo Takabayashi, *Idenshi Igaku* (Gene & Medicine), Vol. 5, No. 3, 2001, pp. 10 to 11 or Haruo Takabayashi, *Idenshi Igaku* (Gene & Medicine), Vol. 5, No. 3, 2001, pp. 28-34. When the obtained fraction containing highly concentrated nucleated red blood cells is applied to a glass slide to prepare a smear sample and an image thereof is prepared, the number of glass slides to be prepared is reduced compared with that required for a conventional technique. Since the samples are not substantially contaminated with white blood cells, nucleated red blood cells can be easily found. Accordingly, the time required for identifying the nucleated red blood cells can be significantly shortened when nucleated red blood cells are to be discovered via visual inspection or with the use of software. For example, the duration can be reduced to 10 times less the amount of time required for a conventional technique.

The technique for conducting DNA analysis of a fetus with the use of the fraction containing fetal nucleated red blood cells obtained from the maternal blood is referred to as fetal DNA diagnosis from maternal blood (FDD-MB®).

In general, the blood cell density naturally changes with the elapse of time after the maternal blood is sampled, and the number of white blood cells in the density range same as that of the nucleated red blood cells increases. When conventional density-gradient centrifugation is performed, the number of white blood cells contaminating a fraction containing nucleated red blood cells increases with the elapse of time. According to the method of the present invention, the density of the nucleated red blood cells can be selectively differentiated from the density range of white blood cells. This can prolong the storage period of the blood sample before the initiation of processing after blood sampling. The present invention also includes a method for prolonging the blood sample storage period.

The present invention includes a kit used for separating and collecting nucleated red blood cells from the maternal blood. The method for separating and collecting nucleated red blood cells from the maternal blood can be implemented with the use of such kit.

The kit comprises a medium for the first density-gradient centrifugation that is isosmotic with nucleated red blood cells, a solution that selectively changes the density of the nucleated red blood cells from that of white blood cells, and a medium for the second density-gradient centrifugation. The solution that selectively changes the density of the nucleated red blood cells from that of white blood cells can also serve as a medium for the second density-gradient centrifugation. A solution used for changing the density of fetal nucleated red blood cells from that of maternal white blood cells can be a solution that is hypertonic to nucleated red blood cells, for example. Alternatively, a solution of a substance capable of changing the density of the nucleated red blood cells through binding may be used. A medium for the first density-gradient centrifugation is isosmotic with nucleated red blood cells, and a medium for the second density-gradient centrifugation is preferably isosmotic with a solution for hypertonic treatment. Examples of substances capable of changing the density of the nucleated red blood cells include dextran and derivatives thereof. An example of dextran is dextran 500, and examples of dextran derivatives include dextran sulfate and carboxymethyl dextran. A dextran solution may comprise dextran at a concentration of 1 to 20% (w/v), and preferably 2 to 15% (w/v) in a mixture thereof with a fraction containing nucleated red blood cells, for example.

A medium used for density-gradient centrifugation can be, for example, Percoll (a colloidal silica product coated with polyvinyl pyrrolidone), Ficoll (a sucrose-epichlorohydrin copolymer), sucrose, Nycodenz® (N,N'-bis(2,3-dihydroxypropyl)-5-[N-(2,3-dihydroxypropyl)acetamido]-2,4-6-triiodo-isophthalamide), or OPTIPrep™ (an aqueous solution of 60% iodixanol). Commercial products, such as Percoll™ (Sigma-Aldrich Japan K. K.), Ficoll™-Paque PLUS, Ficoll-Hypaque (Pharmacia Biotech, Inc.), Histopaque (Sigma-Aldrich Japan K.K.), and Lymphoprep® (Nikomed), can be used as Percoll and Ficoll, respectively. The osmotic pressure of such medium for density-gradient centrifugation can be regulated with the addition of an NaCl solution or via other means. The osmotic pressure of a solution that is isosmotic with nucleated red blood cells is the same as that of physiological saline, which is about 280 mOsm. The density of such medium can also be adequately regulated.

When Percoll is used as a medium for the first density-gradient centrifugation, for example, a 1.070 g/ml Percoll solution and a 1.095 g/ml Percoll solution may be used. Thus, nucleated red blood cells would be present in an intermediate layer therebetween after density-gradient centrifugation. If, for example, a 1.095 g/ml Percoll solution is used alone without performing superposition, nucleated red blood cells would be present on the medium surface.

Examples of solutions that are hypertonic to nucleated red blood cells and used for selectively changing the density of the nucleated red blood cells from that of white blood cells include a sodium chloride solution and a sucrose solution. In this case, a hypertonic solution with an osmotic pressure higher than 280 mOsm may be used. For example, it is 300 mOsm or higher, preferably 308 mOsm or higher, and more preferably 310 mOsm or higher. More specifically, it is 300 to 330 mOsm, preferably 308 mOsm to 330 mOsm, and more preferably 310 to 330 mOsm. Alternatively, it may be 350 to 600 mOsm, and more preferably 400 to 450 mOsm. Specific examples include solutions with a sodium chloride content exceeding 0.9%, preferably of 1.0% to 2.0%, and more preferably of 1.0% to 1.5%.

As a medium for the second density-gradient centrifugation, the medium that can be used for the first density-gradient centrifugation may be used by adequately regulating the osmotic pressure and the density. Also, a solution that selectively changes the density of the nucleated red blood cells from that of the white blood cells may be a medium used for the second density-gradient centrifugation. An example of a medium for the second density-gradient centrifugation that can be used is Polymorphprep™ (AXIS-SHIELD). Polymorphprep is a medium containing 13.8% (w/v) sodium diatrizoate and 8.0% (w/v) dextran 500. The osmotic pressure thereof is 460±15 mOsm, and the density is 1.113+0.001 g/ml at 20° C. Also, Percoll, Ficoll, sucrose, Nycodenz®, OPTIPrep™, and the like may be used while regulating the osmotic pressure.

Further, the kit of the present invention can prolong the storage period of the blood sample before the initiation of processing after blood sampling. The present invention also includes a kit for prolonging the storage period of the blood sample.

The present invention is described in greater detail with reference to the following examples, although the present invention is not limited thereto.

Example 1

Determination of Nucleated Red Blood Cell Density

Figure 2:
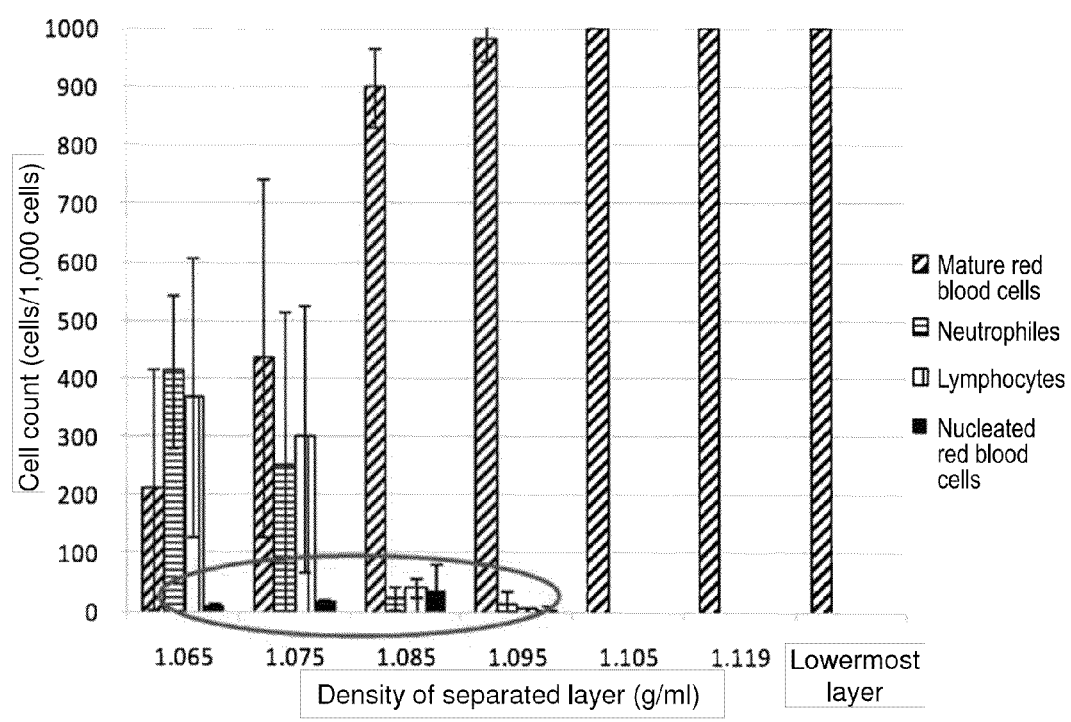
FIG. 2 shows the results attained by subjecting the umbilical cord blood to density-gradient centrifugation and counting the number of blood cells in each phase at various densities.

In Example 1, the umbilical cord blood containing large quantities of nucleated red blood cells was used as a sample. The "umbilical cord blood" is the blood of a fetus collected from the umbilical cord at the time of birth, and it contains large quantities of nucleated red blood cells. In order to inspect the effectiveness of the method of the present invention, the umbilical cord blood containing large quantities of fetal nucleated red blood cells was used, instead of the peripheral blood obtained from a pregnant woman containing small quantities of fetal nucleated red blood cells. The number of nucleated red blood cells in the maternal blood, which is the peripheral blood obtained from a pregnant woman, is lower than that in the umbilical cord blood. According to the method of concentrating and collecting nucleated red blood cells from the umbilical cord blood sample, nucleated red blood cells can be concentrated and collected from the maternal blood. A Percoll stock solution (1.132 g/ml, GE Healthcare Biosciences, Cat. No: 17-0891-01) was used to form a gradient from 1.065 g/ml to 1.119 g/ml, and density-gradient centrifugation was carried out. Cell layers between layers were sampled, and the numbers of mature red blood cells, neutrophiles, lymphocytes, and nucleated red blood cells in cell layers were counted. FIG. 2 shows the results thereof.

Nucleated red blood cells were contained in layers with density ranging from 1.065 to 1.095 g/ml.

Example 2

Separation of Nucleated Red Blood Cells Using Percoll Solution And Polymorphprep Solution Preparation of Percoll Solution and Polymorphprep Solution A Percoll stock solution (4.848 ml, 1.132 g/ml, GE Healthcare Biosciences, Cat. No: 17-0891-01), 1.000 ml of 1.5 M NaCl, and 4.152 ml of sterile water were mixed (total amount: 10.000 ml), an isosmotic Percoll solution (280 mOsm) having a density of 1.070 g/ml was prepared, 6.742 ml of a Percoll stock solution, 1.000 ml of 1.5 M NaCl, and 2.258 ml of sterile water were mixed (total amount: 10.000 ml), and an isosmotic Percoll solution having a density of 1.095 g/ml was prepared.

A Polymorphprep stock solution (8.348 ml, 1.113 g/ml, AXIS-SHIELD, Cat. No: 1114683) and 1.652 ml of 0.9% NaCl were mixed (total amount: 10.000 ml), and a Polymorphprep (PMP) solution having a density of 1.095 g/ml was prepared.

An agreement was obtained from a pregnant woman at the time of delivery and the umbilical cord blood after delivery was used as a sample.

Separation Using Percoll Solution

Figure 3:
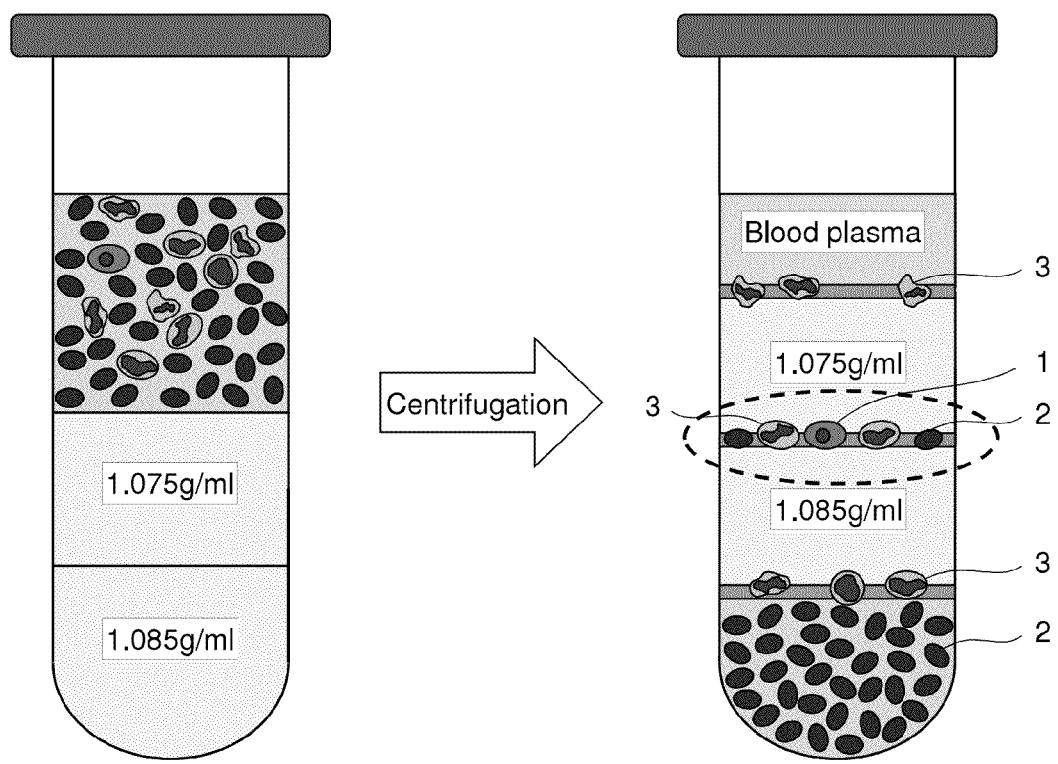
FIG. 3 shows the state of cell separation resulting from density-gradient centrifugation of the maternal blood carried out using a Percoll solution.

The umbilical cord blood (1 ml) was diluted two-fold with 1 ml of 0.9% NaCl. A 1.095 g/ml Percoll solution (2 ml) was introduced into a 15-ml conical tube. With the use of a transfer pipette, 2 ml of the 1.070 g/ml Percoll solution was superposed. The two-fold diluted umbilical cord blood (2 ml) was superposed. Centrifugation was carried out at 20° C. and 3,000 rpm (1,750 G) for 30 minutes. Maternal mature red blood cells and white blood cells with a high density are mainly deposited, and white blood cells with a low density are present on the surface. In fact, a fraction containing nucleated red blood cells is contaminated with some maternal white blood cells. For the purpose of comparison, density-gradient centrifugation was carried out using a Percoll solution alone. In this case, a 1.085 g/ml Percoll solution and a 1.075 g/ml Percoll solution were superposed. FIG. 3 shows the principle of separation carried out with the use of Percoll. FIG. 3 shows a case involving the use of a 1.085 g/ml Percoll solution and a 1.075 g/ml Percoll solution superposed on top of each other. In FIG. 3, nucleated red blood cells are contained in a layer between the 1.075 g/ml layer and the 1.085 g/ml layer shown in the diagram on the right.

Washing after Percoll Treatment

An intermediate layer between the 1.095 g/ml Percoll solution and the 1.070 g/ml Percoll solution (near the boundary) was collected using a micropipette (i.e., a layer containing nucleated red blood cells) and transferred to another 15-ml conical tube. The content of the tube was diluted to 15 ml with the addition of 0.9% NaCl, a suspension was prepared, and the resultant was centrifuged at 20° C. and 1,500 rpm (440 G) for 5 minutes (FAST→FAST), followed by supernatant aspiration. A similar operation was repeated, and washing was carried out twice.

Separation Using PMP

Figure 4:
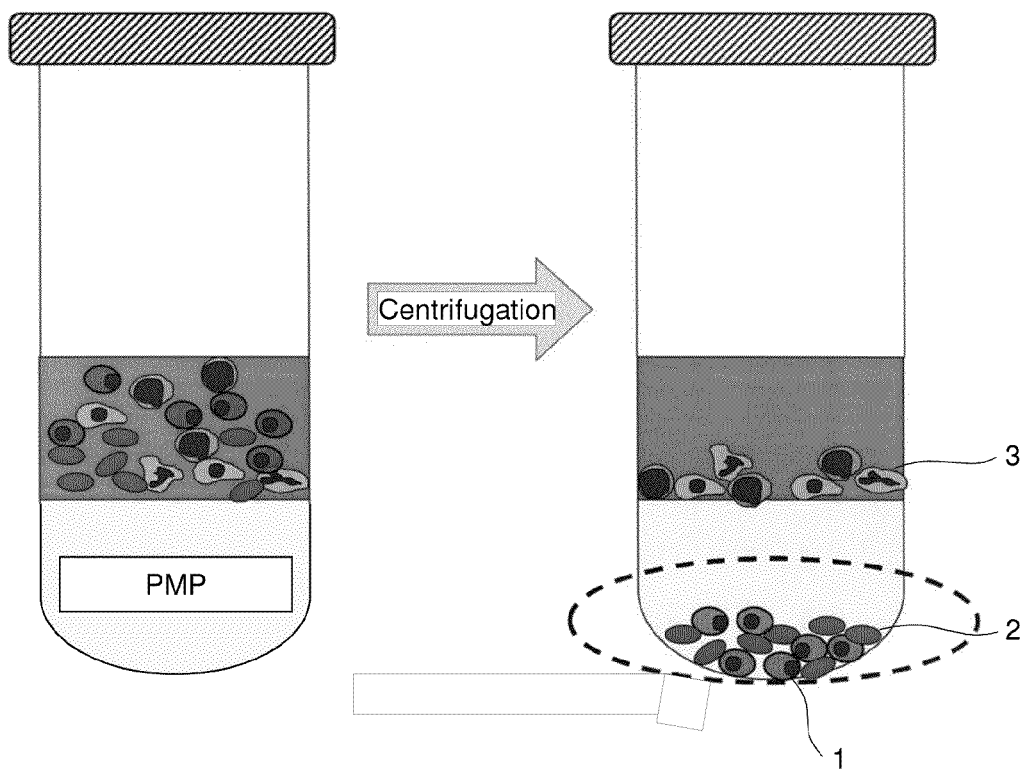
FIG. 4 shows the state of cell separation resulting from density-gradient centrifugation of a fraction containing nucleated red blood cells carried out with the use of a Percoll solution and then with a Polymorphprep solution.

The supernatant was aspirated, the remnant was diluted to 1 ml with the addition of 0.9% NaCl, and a suspension was prepared. The 1.095 g/ml PMP solution (2 ml) was introduced into a round-bottom centrifuge tube, and a sample was superposed. Centrifugation was initiated 20 minutes after sample superposition. Centrifugation was carried out at 20° C. and 2,000 rpm (780 G) for 30 minutes (SLOW→SLOW). FIG. 4 shows the state of cell separation. Nucleated red blood cells are precipitated together with the maternal mature red blood cells contaminating the same. White blood cells exist in a layer with a density lower than that of the layer in which nucleated red blood cells exist. Thus, nucleated red blood cells can be almost completely separated from white blood cells.

Washing after Separation Using PMP

The lowermost layer (i.e., a layer containing nucleated red blood cells and red blood cells) was collected using a micropipette and transferred to another 15-ml conical tube. The content of the tube was diluted to 15 ml with the addition of 0.9% NaCl, a suspension was prepared, and the resultant was centrifuged at 20° C. and 1,500 rpm (440 G) for 5 minutes (FAST→FAST), followed by supernatant aspiration. A similar operation was repeated, and washing was carried out twice.

The sample was adequately diluted with the addition of 0.9% NaCl, and a smear sample was prepared and subjected to May-Grunwald Giemsa staining.

Red blood cell (RBC) lysis buffer was added to the obtained fraction containing nucleated red blood cells to destroy red blood cells, and the number of remaining white blood cells was counted using a hemacytometer. A blood sample obtained on the same day, a blood sample stored for 1 day after blood sampling, and a blood sample stored for 2 days after blood sampling were used.

Figure 5:
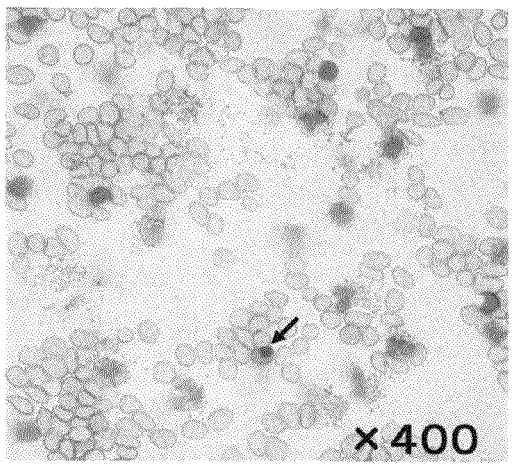
FIG. 5A shows a stained image of a fraction containing nucleated red blood cells obtained via density-gradient centrifugation using a Percoll solution.
FIG. 5B shows the results of May-Grunwald Giemsa staining of a fraction containing nucleated red blood cells obtained via density-gradient centrifugation carried out with the use of a Percoll solution and then with a Polymorphprep solution.
Figure 5:
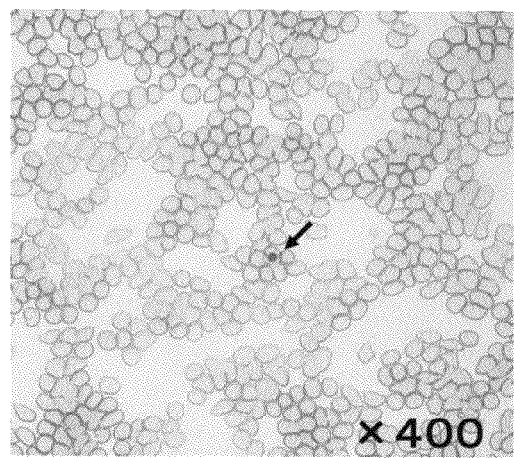

FIG. 5A shows a stained image of a fraction containing nucleated red blood cells obtained via density-gradient centrifugation using a Percoll solution. FIG. 5B shows the results of May-Grunwald Giemsa staining of a fraction containing nucleated red blood cells obtained via density-gradient centrifugation carried out with the use of a Percoll solution and then with a Polymorphprep solution. In the figure, nucleated red blood cells are indicated by arrows. In FIG. 5A, stained cells other than the nucleated red blood cells are white blood cells. Other cells shown in FIG. 5A and FIG. 5B are maternal red blood cells.

As shown in FIG. 5A, the fraction containing nucleated red blood cells was contaminated with large quantities of white blood cells as a result of density-gradient centrifugation using a Percoll solution alone. When density-gradient centrifugation was carried out with the use of a Percoll solution and then with a Polymorphprep solution, however, no white blood cells were observed in the fraction.

Figure 6:
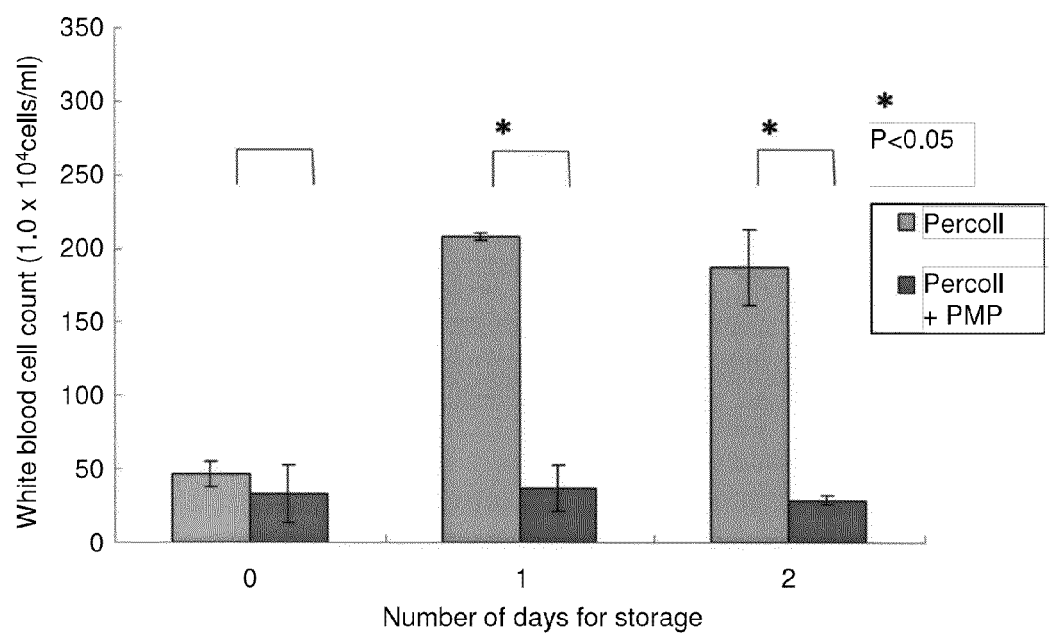
FIG. 6 shows the number of white blood cells contaminating a nucleated red blood cell fraction based on the number of days of storage.

FIG. 6 shows the number of white blood cells that contaminate a fraction of nucleated red blood cells based on the number of days of storage. The results of measurement of white blood cell counts are shown. In the fraction obtained via density-gradient centrifugation carried out with the use of a Percoll solution and then with a Polymorphprep solution, the percentages of white blood cells decrease were 28% in the blood sample obtained on the same day, 82% in the blood sample stored for 1 day, and 84% in the blood sample stored for 2 days, compared with the fraction obtained via density-gradient centrifugation using a Percoll solution alone. The results demonstrate that, when density-gradient centrifugation is carried out using a Percoll solution alone, the number of white blood cells contaminating the fraction containing nucleated red blood cells increases with the storage of sampled blood. When density-gradient centrifugation is carried out with the use of a Percoll solution and then with a Polymorphprep solution, however, the number of white blood cells contaminating the fraction containing nucleated red blood cells does not increase with the storage of the sampled blood. When the blood is stored, the white blood cell density may vary, and the density of the white blood cells may overlap that of the nucleated red blood cells to a greater degree. Even under such circumstances, nucleated red blood cells can be effectively separated from white blood cells according to the method of the present invention.

Figure 7:
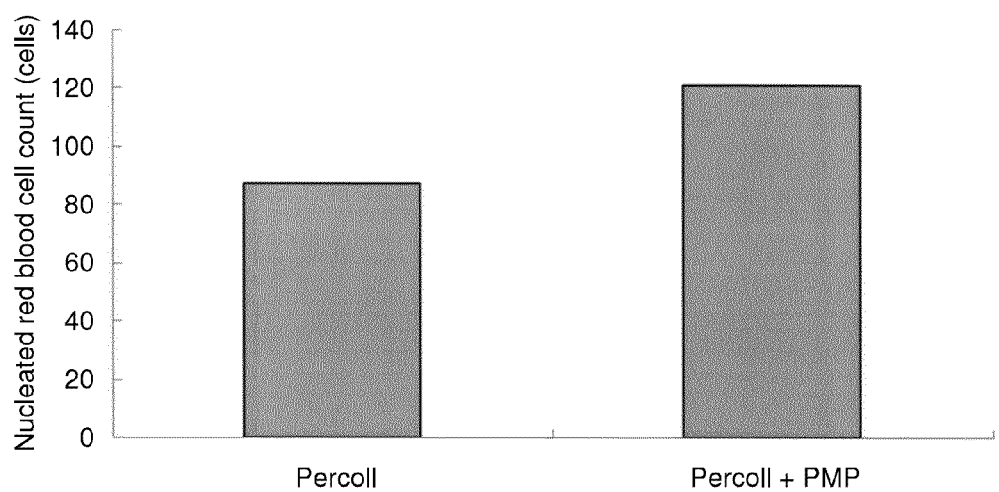
FIG. 7 shows a comparison of the number of nucleated red blood cells collected when density-gradient centrifugation is carried out using a Percoll solution alone and when density-gradient centrifugation is carried out with the use of a Percoll solution and then with a Polymorphprep solution.

FIG. 7 shows the results of measurement of nucleated red blood cell counts after May-Grunwald Giemsa staining.

As shown in FIG. 7, the number of nucleated red blood cells collected via density-gradient centrifugation with the use of a Percoll solution (fractions to be collected: 1.070 to 1.095 g/ml) and then with a Polymorphprep solution (the Percoll method and the PMP method) was 1.4 times greater than that obtained via density-gradient centrifugation using a Percoll solution alone (the Percoll method) (fractions to be collected: 1.075 to 1.085 g/ml).

When conducting density-gradient centrifugation using a Percoll solution, it is necessary to expand the density range in order to collect large quantities of nucleated red blood cells. This would disadvantageously increase the number of contaminating white blood cells. When density-gradient centrifugation is carried out with the use of a Percoll solution and then with a Polymorphprep solution, however, nucleated red blood cells can be separated from white blood cells via density-gradient centrifugation with the use of a Polymorphprep solution even if the fraction is contaminated with white blood cells due to an expanded density range of cell layers to be collected in the first step of density-gradient centrifugation with the use of a Percoll solution.

Example 3

Separation of Nucleated Red Blood Cells Using Percoll Solution and NaCl Solution Preparation of Isosmotic Percoll Solution and Hypertonic Percoll Solution A Percoll stock solution (4.848 ml), 1.000 ml of 1.5 M NaCl, and 4.152 ml of sterile water were mixed (total amount: 10.000 ml) to prepare an isosmotic Percoll solution (280 mOsm) having a density of 1.070 g/ml. A Percoll stock solution (6.742 ml), 1.000 ml of 1.5 M NaCl, and 2.258 ml of sterile water were mixed (total amount: 10.000 ml) to prepare an isosmotic Percoll solution having a density of 1.095 g/ml.

Further, 6.529 ml of a Percoll stock solution, 1.470 ml of 1.5 M NaCl, and 2.0011 ml of sterile water were mixed (total amount: 10.000 ml) to prepare a hypertonic Percoll solution (420 mOsm) having a density of 1.095 g/ml.

An agreement was obtained from a pregnant woman at the time of delivery, and the umbilical cord blood after delivery was used as a sample.

Separation with Isosmotic Percoll Solution

The umbilical cord blood (1 ml) was diluted two-fold with the addition of 1 ml of 0.9% NaCl. The 1.095 g/ml Percoll solution (2 ml) was introduced into a 15-ml conical tube. With the use of a transfer pipette, 2 ml of the 1.070 g/ml Percoll solution was superposed. The two-fold diluted maternal blood (2 ml) was superposed. The resultant was centrifuged at 20° C. and 3,000 rpm (1750 G) for 30 minutes (SLOW→SLOW).

An intermediate layer between the 1.095 g/ml Percoll solution and the 1.070 g/ml Percoll solution (near the boundary) was collected using a micropipette (i.e., a layer containing nucleated red blood cells) and transferred to another 15-ml conical tube. The content of the tube was diluted to 15 ml with the addition of 0.9% NaCl, a suspension was prepared, and the resultant was subjected to centrifugation at 20° C. and 1,500 rpm (440 G) for 5 minutes (FAST→FAST), followed by supernatant aspiration. A similar operation was repeated, and washing was carried out twice.

After washing, the second density-gradient centrifugation was carried out under conditions A to D below.

Under any of conditions A to D, the osmotic pressure of the medium used for the first density-gradient centrifugation was 280 mOsm, and that of the medium used for the second density-gradient centrifugation was 420 mOsm.

A: After a suspension of the sample in 0.9% NaCl was prepared, the second density-gradient centrifugation was carried out using a Polymorphprep solution.

After washing, the supernatant was aspirated. The remnant was diluted to 1 ml with the addition of 0.9% NaCl, and a suspension was prepared. The 1.095 g/ml Polymorphprep solution (2 ml) was introduced into a round-bottom centrifuge tube, and the sample was superposed. Centrifugation was carried out at 20° C. and 2,000 rpm (780 G) for 30 minutes (SLOW→SLOW). Centrifugation was initiated 20 minutes after sample superposition.

B: After a suspension of the sample in 0.9% NaCl was prepared, the second density-gradient centrifugation was carried out using a Percoll solution.

After washing, the supernatant was aspirated. The remnant was diluted to 1 ml with the addition of 0.9% NaCl, and a suspension was prepared. The 1.095 g/ml hypertonic Percoll solution (420 mOsm) (2 ml) was introduced into a round-bottom centrifuge tube and the sample was superposed. Centrifugation was carried out at 20° C. and 2,000 rpm (780 G) for 30 minutes (SLOW→SLOW).

C: After a suspension of the sample in 0.9% NaCl was prepared, the second density-gradient centrifugation was carried out using a mixture of a hypertonic Percoll solution and a Polymorphprep solution.

After washing, the supernatant was aspirated. The remnant was diluted to 1 ml with the addition of 0.9% NaCl, and a suspension was prepared. A solution (2 ml) of the 1.095 g/ml hypertonic Percoll solution (420 mOsm) mixed with the 1.095 g/ml Polymorphprep solution at a ratio of 1:1 by volume was introduced into a round-bottom centrifuge tube, and the sample was superposed. Centrifugation was carried out at 20° C. and 2,000 rpm (780 G) for 30 minutes (SLOW→SLOW).

D: After a suspension of the sample in 1.3% NaCl was prepared, the second density-gradient centrifugation was carried out using a Polymorphprep solution.

After washing, the supernatant was aspirated. The remnant was diluted to 1 ml with the addition of 1.39% NaCl, and a suspension was prepared. The 1.095 g/ml Polymorphprep solution (2 ml) was introduced into a round-bottom centrifuge tube and the sample was superposed. Centrifugation was carried out at 20° C. and 2,000 rpm (780 G) for 30 minutes (SLOW→SLOW). Centrifugation was initiated 20 minutes after sample superposition.

Washing after Second Density-Gradient Centrifugation

The lowermost layer (i.e., a layer containing nucleated red blood cells and red blood cells) was collected using a micropipette and transferred to another 15-ml conical tube. The content of the tube was diluted to 15 ml with the addition of 0.9% NaCl, a suspension was prepared, and the resultant was subjected to centrifugation at 20° C. and 1,500 rpm (440 G) for 5 minutes (FAST→FAST), followed by supernatant aspiration. A similar operation was repeated, and washing was carried out twice.

The sample was adequately diluted with the addition of 0.9% NaCl, and a smear sample was prepared on a glass slide and subjected to May-Grunwald Giemsa staining.

Substantially no white blood cells were observed in the fraction containing nucleated red blood cells obtained under any of conditions A to D above. Also, the total numbers of blood cells on the glass slides were substantially the same. The numbers of nucleated red blood cells on a single glass slide were equivalent to one another under conditions A, B, C, and D (i.e., 222, 213, 277, and 257, respectively).

Figure 8:
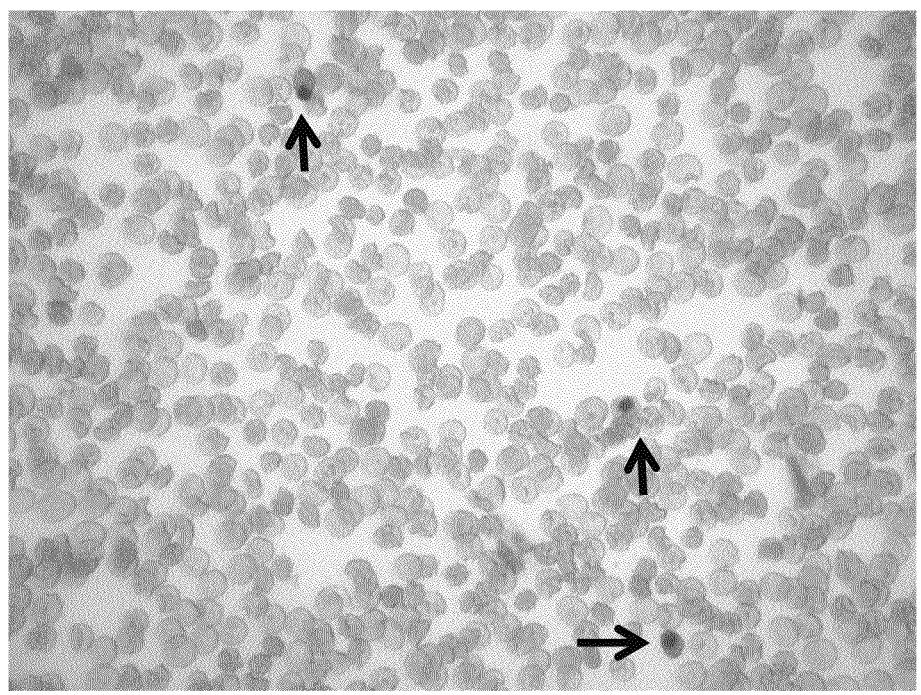
FIG. 8 shows an image obtained via May-Grunwald Giemsa staining of a fraction containing nucleated red blood cells obtained via density-gradient centrifugation with the use of an isosmotic Percoll solution and then with a hypertonic Percoll solution.

FIG. 8 shows the results of May-Grunwald Giemsa staining of a fraction containing nucleated red blood cells obtained via density-gradient centrifugation with the use of an isosmotic Percoll solution and then with a hypertonic Percoll solution (B above). In FIG. 8, nucleated red blood cells are indicated with arrows. As shown in FIG. 8, substantially no white blood cells were observed in the obtained fraction, and mature red blood cells and nucleated red blood cells derived from the mother were observed. As shown in the figure, mature red blood cells can be easily distinguished from nucleated red blood cells based on nuclear staining.

Based on the results attained in Example 3, concentrated nucleated red blood cells in the maternal blood were found to be collected by regulating the densities of a medium used for the first density-gradient centrifugation and of a medium used for the second density-gradient centrifugation and the osmotic pressure thereof.

Example 4

Separation from Maternal Blood

Figure 9:
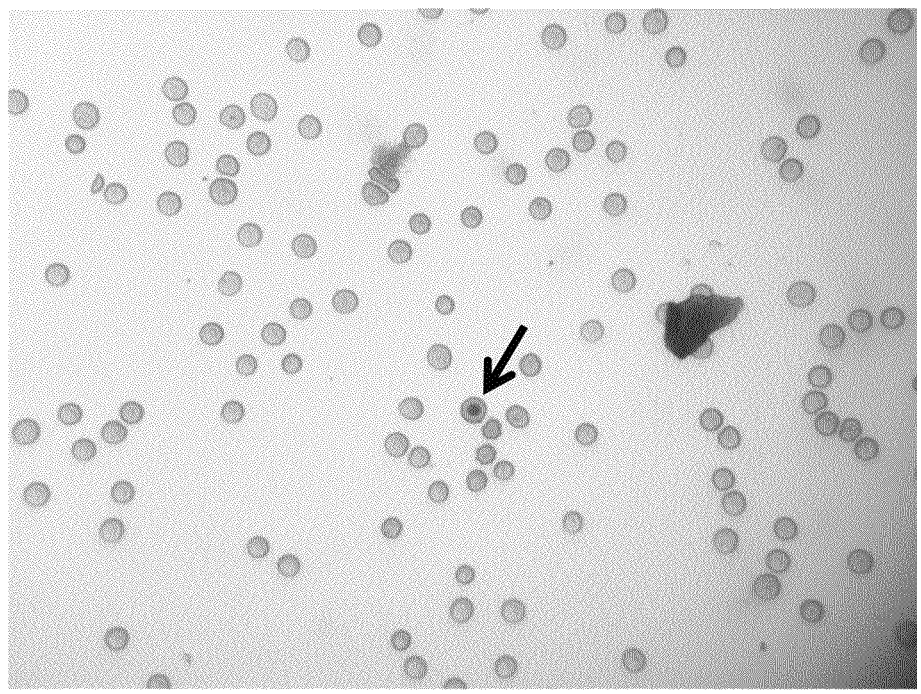
FIG. 9 shows an image obtained via May-Grunwald Giemsa staining of a fraction containing nucleated red blood cells obtained via density-gradient centrifugation of the maternal blood with the use of a Percoll solution and then with a Polymorphprep solution.

Nucleated red blood cells were separated from the maternal blood (the peripheral blood obtained from a pregnant woman) by the separation method (condition B) using the isosmotic Percoll solution and the hypertonic Percoll solution described in Example 3. While the number of nucleated red blood cells was very low in the maternal blood, these cells were found to be separable by the method of the present invention. FIG. 9 shows the results of May-Grunwald Giemsa staining of a fraction containing nucleated red blood cells obtained via density-gradient centrifugation of the maternal blood with the use of a Percoll solution and then with a Polymorphprep solution.

Example 5

Separation of Nucleated Red Blood Cells Using Isosmotic Percoll Solution and Hypertonic Percoll Solution Preparation of Isosmotic Percoll Solution and Hypertonic Percoll Solution A Percoll stock solution (4.848 ml), 1.000 ml of 1.5 M NaCl, and 4.152 ml of sterile water were mixed (total amount: 10.000 ml) to prepare an isosmotic Percoll solution (280 mOsm) having a density of 1.070 g/ml. A Percoll stock solution (6.742 ml), 1.000 ml of 1.5 M NaCl, and 2.258 ml of sterile water were mixed (total amount: 10.000 ml) to prepare an isosmotic Percoll solution having a density of 1.095 g/ml.

Further, 32.59 ml of a Percoll stock solution, 5.20 ml of 1.5 M NaCl, and 12.21 ml of sterile water were mixed (total amount: 50.000 ml) to prepare a hypertonic Percoll solution (312 mOsm) having a density of 1.090 g/ml.

Further, 32.48 ml of a Percoll stock solution, 5.45 ml of 1.5 M NaCl, and 12.07 ml of sterile water were mixed (total amount: 50.000 ml) to prepare a hypertonic Percoll solution (330 mOsm) having a density of 1.090 g/ml.

An agreement was obtained from a pregnant woman, and the sampled peripheral blood was used as the maternal blood sample.

Separation Using Isosmotic Percoll Solution (First Step of Density-Gradient Centrifugation)

The maternal blood (1 ml) was diluted two-fold with the addition of 1 ml of 0.9% NaCl. The 1.095 g/ml Percoll solution (2 ml) was introduced into a 15-ml conical tube. With the use of a transfer pipette, 2 ml of the 1.070 g/ml Percoll solution was superposed. The two-fold diluted maternal blood (2 ml) was superposed. The resultant was centrifuged at 20° C. and 3,000 rpm (1750 G) for 30 minutes (SLOW→SLOW).

An intermediate layer between the 1.095 g/ml Percoll solution and the 1.070 g/ml Percoll solution (near the boundary) was collected using a micropipette (i.e., a layer containing nucleated red blood cells) and transferred to another 15-ml conical tube. The content of the tube was diluted to 15 ml with the addition of 0.9% NaCl, a suspension was prepared, and the resultant was subjected to centrifugation at 20° C. and 1,500 rpm (440 G) for 5 minutes (FAST→FAST), followed by supernatant aspiration. A similar operation was repeated, and washing was carried out twice. The above-described operation was carried out with the use of 5 test tubes, and 60 μl of a fraction containing nucleated red blood cells was obtained.

A portion of 5 μl was collected for evaluation, 95 μl of fetal calf serum (FCS) was added (sample: FCS=1:19), a suspension was prepared, and a smear sample was prepared using 2.5 μl thereof on a glass slide and subjected to May-Grunwald Giemsa staining.

Separation Using Hypertonic Percoll Solution (First Step of Density-Gradient Centrifugation)

The sample after Percoll treatment (32.5 μl) was diluted to 1 ml with the addition of 0.9% NaCl. A hypertonic Percoll solution (1.099 g/ml, 330 mOsm) (A) or a hypertonic Percoll solution (1.090 g/ml, 312 mOsm) (B) (2 ml) was introduced into a conical tube, and 1 ml of a sample separated with the use of an isosmotic Percoll solution was superposed. The resultant was centrifuged at 20° C. and 2,000 rpm (780 G) for 30 minutes (SLOW→SLOW).

Washing after Second Step of Density-Gradient Centrifugation

The lowermost layer (i.e., a layer containing nucleated red blood cells and red blood cells) was collected using a micropipette and transferred to another 15-ml conical tube. The content of the tube was diluted to 15 ml with the addition of 0.9% NaCl, a suspension was prepared, and the resultant was centrifuged at 20° C. and 1,500 rpm (440 G) for 5 minutes (FAST→FAST), followed by supernatant aspiration. A similar operation was repeated, and washing was carried out twice.

The above-described operation was carried out with the use of 5 test tubes, and 30 μl of a fraction containing nucleated red blood cells was obtained when the hypertonic Percoll solution (1.099 g/ml, 330 mOsm) was used (A) or when the hypertonic Percoll solution (1.090 g/ml, 312 mOsm) was used (B). A portion of 5 μl was collected for evaluation, 96 μl of FCS was added (sample: FCS=1:19), a suspension was prepared, and a smear sample was prepared using 2.5 μl thereof on a glass slide and subjected to May-Grunwald Giemsa staining. The above-described method was carried out with the use of a hypertonic Percoll solution with an osmotic pressure of 312 mOsm or 330 mOsm. In addition, the maternal blood was used to carry out the second density-gradient centrifugation with the use of a hypertonic Percoll solution with an osmotic pressure of 308 mOsm, 322 mOsm, 353 mOsm, or 383 mOsm. Volumes of the collected fractions containing nucleated red blood cells and NRBC concentrations varied depending on the experiment.

The number of white blood cells in the sample obtained via the second density-gradient centrifugation using a hypertonic Percoll solution relative to the number of white blood cells in the sample obtained via the first density-gradient centrifugation using an isosmotic Percoll solution was determined via microscopic observation. The percentage of white blood cells in the sample obtained via the first density-gradient centrifugation removed through the second density-gradient centrifugation was calculated and expressed as the white blood cell (WBC) removal percentage. FIG. 10 shows the results thereof. FIG. 10 shows experimental runs, blood samples used, the presence/absence of a band of white blood cells after the second density-gradient centrifugation (a band was removed if it appeared), and the percentage of white blood cells removed with the use of Percoll solutions at various osmotic pressure levels as the hypertonic Percoll solutions. The white blood cell removal percentage is preferably 90% or higher, more preferably 95% or higher, further preferably 97% or higher, still further preferably 98% or higher, and particularly preferably 99% or higher.

When the osmotic pressure of the hypertonic Percoll solution used for the second density-gradient centrifugation was 310 to 330 mOsm, the WBC removal percentage was high.

The results demonstrate that nucleated red blood cells can be collected at high density when the osmotic pressure of the hypertonic Percoll solution used for the second density-gradient centrifugation is 310 to 330 mOsm.

INDUSTRIAL APPLICABILITY

The present invention enables concentration and collection of fetal nucleated red blood cells from the maternal blood, gene and chromosome analysis of a fetus with the use of the collected nucleated red blood cells, and easy prenatal genetic diagnosis.

DESCRIPTION OF NUMERAL REFERENCES

1: Nucleated red blood cells
2: Red blood cells
3: White blood cells

All publications, patents, and patent applications cited herein are incorporated herein by reference in their entirety.

The invention claimed is:

1. A method for concentrating and collecting nucleated red blood cells from maternal blood comprising:
   (i) subjecting the maternal blood to a first density-gradient centrifugation and collecting a cell fraction containing nucleated red blood cells;
   (ii) treating the cell fraction containing nucleated red blood cells to selectively change the density of the nucleated red blood cells to be greater than 1.095 g/ml, so as not to overlap that of white blood cells in the cell fraction, by discharging water from the nucleated red blood cells using a solution that is hypertonic to nucleated red blood cells; and
   (iii) subjecting the treated cell fraction containing the nucleated red blood cells to a second density-gradient centrifugation so as to collect a fraction containing nucleated red blood cells.

2. The method for concentrating and collecting nucleated red blood cells according to claim 1, wherein a solution capable of selectively changing the density of the nucleated red blood cells is used as a medium for the second density-gradient centrifugation and step (ii) is carried out simultaneously with step (iii).

3. The method for concentrating and collecting nucleated red blood cells according to claim 1, wherein blood cells with a density range of 1.070 to 1.095 g/ml are collected in step (i).

4. The method for concentrating and collecting nucleated red blood cells according to claim 1, wherein
   the medium used for the first density gradient centrifugation is selected from the group consisting of colloidal silica coated with polyvinyl pyrrolidone, sucrose-epichlorohydrin copolymer, sucrose, N,N'-bis(2,3-dihydroxypropyl)-5-[N-(2,3-dihydroxypropyl)acetamido]-2,4-6-tri-iodo-isophthalamide, and an aqueous solution of 60% iodixanol, and
   the medium used for the second density gradient centrifugation is selected from the group consisting of colloidal silica coated with polyvinyl pyrrolidone, sucrose-epichlorohydrin copolymer, sucrose, N,N'-bis(2,3-dihydroxypropyl)-5-[N-(2,3-dihydroxypropyl)acetamido]-2,4-6-tri-iodo-isophthalamide, an aqueous solution of 60% iodixanol, and a medium containing 13.8% (w/v) sodium diatrizoate and 8.0% (w/v) dextran 500.

5. The method for concentrating and collecting nucleated red blood cells according to claim 1, wherein the medium used for the first density-gradient centrifugation is colloidal silica coated with polyvinyl pyrrol having an osmotic pressure of 280±30 mOsm and the medium used for the second density-gradient centrifugation is colloidal silica coated with polyvinyl pyrrol having an osmotic pressure of 300 mOsm or higher.

6. The method for concentrating and collecting nucleated red blood cells according to claim 1, wherein the medium used for the first density-gradient centrifugation is colloidal silica coated with polyvinyl pyrrol and the medium used for the second density-gradient centrifugation is a medium containing 13.8% (w/v) sodium diatrizoate and 8.0% (w/v) dextran 500.

7. The method for concentrating and collecting nucleated red blood cells according to claim 1, wherein the nucleated red blood cells are derived from a fetus.

* * * * *